US012697082B2

(12) United States Patent
Kim

(10) Patent No.: US 12,697,082 B2
(45) Date of Patent: Aug. 4, 2026

(54) LASER LINE PROJECTOR FOR LATERAL CEPHALOGRAMS DIGITAL RADIOGRAPHY

(71) Applicant: Il Gon Kim, Gwangju (KR)

(72) Inventor: Il Gon Kim, Gwangju (KR)

( * ) Notice: Subject to any disclaimer, the term of this patent is extended or adjusted under 35 U.S.C. 154(b) by 0 days.

(21) Appl. No.: 18/764,344

(22) Filed: Jul. 4, 2024

(65) Prior Publication Data

US 2025/0009317 A1      Jan. 9, 2025

(30) Foreign Application Priority Data

Jul. 7, 2023      (KR) ......................... 10-2023-0088652

(51) Int. Cl.
*A61B 6/50*          (2024.01)
*A61B 6/04*          (2006.01)

(52) U.S. Cl.
CPC ............ *A61B 6/501* (2013.01); *A61B 6/0492* (2013.01)

(58) Field of Classification Search
None
See application file for complete search history.

(56) References Cited

U.S. PATENT DOCUMENTS

2015/0164442 A1* 6/2015 Hirabayashi ............. A61B 6/51
                                                    378/62
2019/0307415 A1* 10/2019 Antikainen .............. A61B 6/08

FOREIGN PATENT DOCUMENTS

KR      1020160056986       5/2016
WO      WO-2013095706 A1 *  6/2013  ............. A61B 6/482

* cited by examiner

*Primary Examiner* — Katherine L Fernandez
(74) *Attorney, Agent, or Firm* — JCIPRNET

(57)                    ABSTRACT

The present invention relates to a laser line projecting device having a new structure, which is provided in a lateral cephalometric radiograph device to check whether a center of a user's face is accurately located on a sagittal plane by vertically or horizontally projecting light onto the user's face.

The laser line projecting device for a lateral cephalometric radiograph device according to the present invention includes a support rod (10) extending downward from a lower surface of the support (1) of the lateral cephalometric radiograph device and a projection unit (20) provided on the support rod (10) and projecting linear light onto the user's face fixed to the ear rod (3), and the projection unit (20) projects a vertical line (21) extending in a vertical direction and a horizontal line (22) extending in a horizontal direction.

Thus, an operator may visually check the vertical line (21) to identify whether a central line of the user's face is accurately located on a sagittal plane, may photograph the head in a state in which the user's head is adjusted to be exactly perpendicular to the left-right direction and the front-rear direction, and thus may obtain an accurate lateral cephalometric image.

2 Claims, 4 Drawing Sheets

LASER LINE PROJECTOR FOR LATERAL CEPHALOGRAMS DIGITAL RADIOGRAPHY

TECHNICAL FIELD

The present invention relates to a laser line projecting device having a new structure, which is provided in a lateral cephalometric radiograph device to check whether a center of a user's face is accurately located on a sagittal plane by vertically or horizontally projecting light onto the user's face.

BACKGROUND ART

FIGS. 1 and 2 illustrate examples of a lateral cephalometric radiograph device commonly used to analyze a face in the field of orthodontics or surgery, and the lateral cephalometric radiograph device includes a support 1, a detector 2 provided to extend downward from one side of the support 1, ear rods 3 provided to extend downward from the support 1 and coupled to both ear holes of a user, and a nasion guide 4 provided to extend downward from a lower side of the support 1 and come into contact with the nasion (upper root portion of the nose) of the user.

The detector 2 is usually referred to as a sensor or a detector and functions to receive radiation output from a generator that is not illustrated.

In the present embodiment, the detector 2 is provided to extend downward from a left side of the support 1, and the generator is located on a right side of the support 1.

The ear rod 3 is formed in a bar shape extending in a vertical direction, and an ear plug 3a coupled to the ear hole of the user is provided at a lower end thereof to extend laterally. When the ear plug 3a is coupled to the ear hole, the heights of both sides of the user's head are adjusted to be the same, thereby supporting the user's head such that the head is not tilted laterally.

The nasion guide 4 is provided to extend downward from a lower front side of the support 1, and a contact part 4a that comes into contact with the nasion of the user is provided at a lower end thereof to extend rearward.

In this case, an upper end of the nasion guide 4 is laterally rotatably coupled to a bracket 4b provided under the support 1.

Thus, in a state in which the ear plug 3a of the ear rod 3 is coupled to the ear hole of the user to adjust the left-right tilt of the user's head, the front-rear tilt of the head is adjusted so that the contact part 4a of the nasion guide 4 comes into contact with the user's nasion and the user's head is accurately perpendicular to the front-rear and left-right directions, and when the generator is operated, the radiation output from the generator passes through a bone of the user and is radiated to the detector 2 so that a structure of the user's bone is photographed.

However, this lateral cephalometric radiograph device couples the ear plug 3a provided on the ear rod 3 to the ear hole of the user to adjust the ear plug 3a such that the left-right tilt of the user's head becomes vertical.

Thus, the heights of both ear holes of the user should be the same, and when the heights of both ear holes are different or positions thereof in the front-rear direction are different, the head tilts.

In this case, an operator operating the lateral cephalometric radiograph device checks whether the user's head is vertical, and when the user's head is tilted left-right or front-rear, the user's head should be adjusted to be vertical. Since there is no way for the operator to check whether the user's head is vertical, the user's head is photographed while laterally tilted. Accordingly, it is difficult to accurately obtain a lateral cephalometric image located on a sagittal plane.

Thus, a new method for solving this problem is required.

RELATED ART DOCUMENT

Patent Document (Patent Document 1) Korean Laid-open Patent No. 10-2016-0056986.

DISCLOSURE

Technical Problem

The present invention is directed to providing a laser line projecting device having a new structure, which is provided in a lateral cephalometric radiograph device and may check whether a central line of a user's face is accurately located on a sagittal plane of the device by vertically or horizontally projecting light onto the user's face.

Technical Solution

There is provided a laser line projecting device for a lateral cephalometric radiograph device, which is provided in the lateral cephalometric radiograph device including a support (1), a detector (2) extending downward from one side of the support (1), and ear rods (3) extending downward from the support (1) and coupled to both ear holes of a user, the laser line projecting device including a support rod (10) extending downward from a lower surface of the support (1), and a projection unit (20) that is provided in the support rod (10) and project linear light onto a face of the user fixed to the ear rods (3), wherein the projection unit (20) projects a vertical line (21) extending in a vertical direction or a horizontal line (22) extending in a horizontal direction.

The support rod (10) may include a fixed block (11) fixed to the lower surface of the support (1), and a rod body (12) extending in the vertical direction and having an upper end detachably coupled to the fixed block (11).

The ear rods (3) may be configured in a bar shape extending in the vertical direction and have ear plugs (3a) coupled to the ear holes of the user and extending in a lateral direction at a lower end thereof, and the projection unit (20) may project the horizontal line (22) such that the horizontal line (22) passes through the center of the ear plugs (3a).

The laser line projecting device may further include a coupling detecting unit (30) that is provided at an upper end of the rod body (12) and detects whether the rod body (12) is coupled to the fixed block (11), a camera (40) that is provided on a lower rear surface of the rod body (12) to face a rear side and photographs the user' face and locations of the vertical line (21) and the horizontal line (22) projected onto the face, and a control unit (50) that is connected to the coupling detecting unit (30) and the camera (40) and controls the operation of the projection unit (20), wherein the control unit (50) may be equipped with an image analysis program (51) for analyzing an image captured by the camera (40) and may turn off the projection unit (20) when it is detected through the coupling detecting unit (30) that the upper end of the body rod (12) is separated from the fixed block (11) or it is detected by analyzing the image captured by the camera (40) that light output from the projection unit (20) is projected to a location close to the user's eyes.

Advantageous Effects

The laser line projecting device for a lateral cephalometric radiograph device according to the present invention includes the support rod (10) extending downward from the lower surface of the support (1) of the lateral cephalometric radiograph device and the projection unit (20) provided on the support rod (10) and projecting linear light onto the user's face fixed to the ear rod (3), and the projection unit (20) projects the vertical line (21) extending in the vertical direction and the horizontal line (22) extending in the horizontal direction.

Thus, the operator can visually identify the vertical line (21) to check whether a central line of the user's face is accurately located on a sagittal plane, can photograph the head in a state in which the user's head is adjusted to be exactly perpendicular to the left-right and front-rear directions, and thus can obtain an accurate lateral cephalometric image.

MODES OF THE INVENTION

Figure 1:
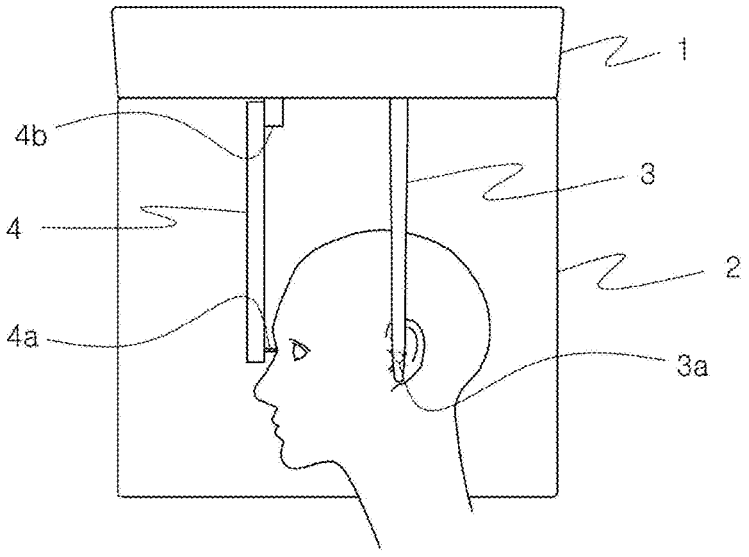
FIG. 1 is a side view illustrating a lateral cephalometric radiograph device according to the related art.
Figure 2:
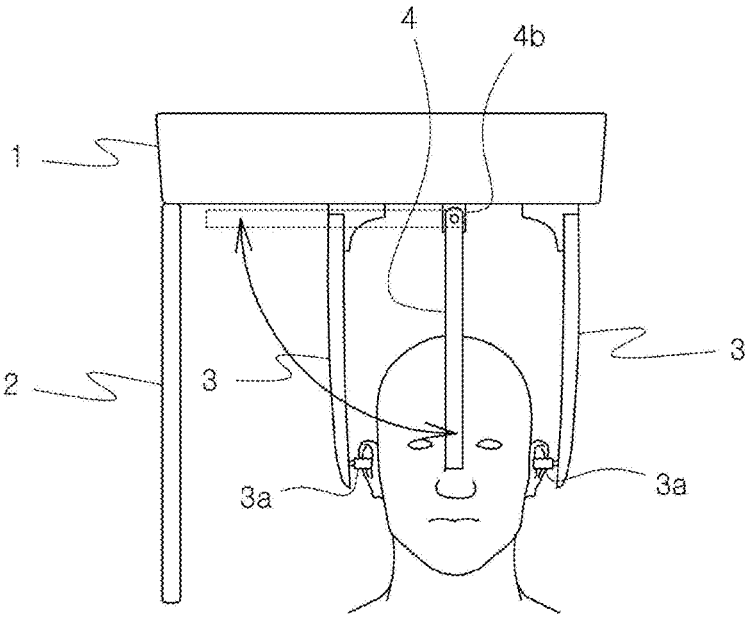
FIG. 2 is a front view illustrating the lateral cephalometric radiograph device according to the related art.
Figure 3:
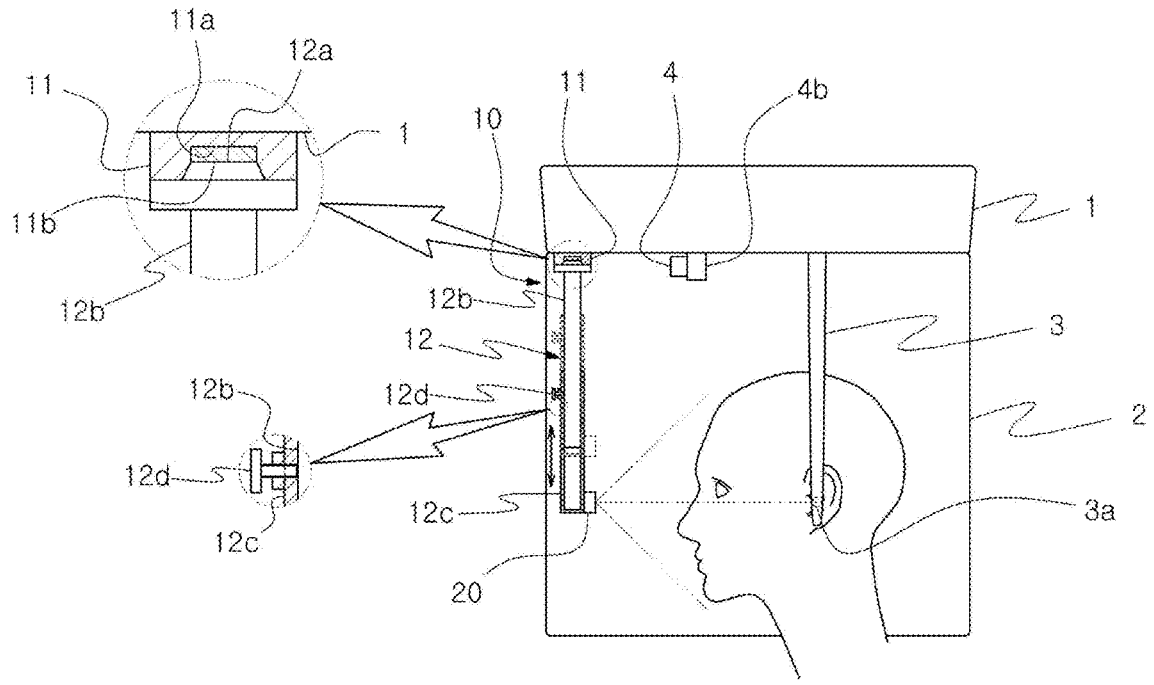
FIG. 3 is a side cross-sectional view illustrating a laser line projecting device for a lateral cephalometric radiograph device according to the present invention.
Figure 4:
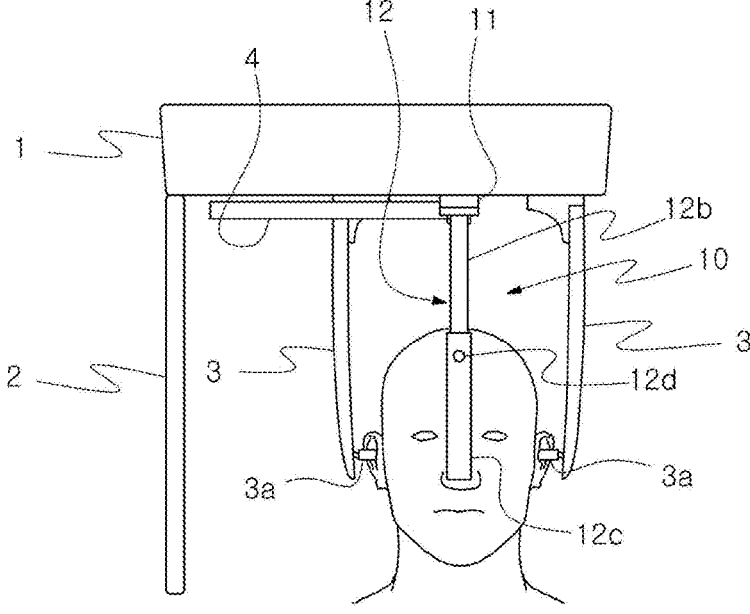
FIG. 4 is a front view illustrating the laser line projecting device for a lateral cephalometric radiograph device according to the present invention.

Hereinafter, the present invention will be described in detail with reference to the accompanying drawings.

FIGS. 3 to 6 illustrate a laser line projecting device for a lateral cephalometric radiograph device according to the present invention, which is provided in the lateral cephalometric radiograph device.

In this case, the lateral cephalometric radiograph device includes a support 1, a detector 2 provided to extend downward from one side of the support 1, ear rods 3 provided to extend downward from the support 1 and coupled to both ear holes of a user, and a nasion guide 4 provided to extend downward from a lower side of the support 1 and come into contact with the user's nasion.

The ear rod 3 is formed in a bar shape extending in a vertical direction, and an ear plug 3a coupled to the ear hole of the user is provided at a lower end thereof to extend laterally.

The nasion guide 4 is provided to extend downward from a lower front side of the support 1, and a contact part 4a that comes into with the user's nasion is provided at a lower end thereof to extend rearward.

In this case, an upper end of the nasion guide 4 is laterally rotatably coupled to a bracket 4b provided under the support 1.

Further, the laser line projecting device according to the present invention includes a support rod 10 extending downward from a lower surface of the support 1 and a projection unit 20 provided on the support rod 10 and projecting linear light onto the user's face fixed to the ear rod 3.

The support rod 10 includes a fixed block 11 fixed to a lower surface of the support 1 and a rod body 12 extending in the vertical direction and having an upper end detachably coupled to the fixed block 11.

The fixed block 11 is fixed to the lower surface of the support 1 to be located in front of the nasion guide 4, a coupling hole 11a is formed in a lower surface thereof, and a magnet 11b is provided inside the coupling hole 11a.

The rod body 12 is formed in the shape of a circular rod extending in the vertical direction, and a coupling part 12a coupled to the coupling hole 11a is provided at an upper end thereof to protrude upward.

In this case, the coupling part 12a includes a magnetic material attached to the magnet 11b, and when the coupling part 12a is inserted into the coupling hole 11a, the fixed block 11 is fixedly coupled to an upper end of the rod body 12 by the magnet 11b.

Further, the rod body 12 may include an upper rod 12b connected to the coupling part 12a, a lower rod 12c coupled to a lower side of the upper rod 12b in a vertically movable manner, and a fixing screw 12d coupled to the lower rod 12c, and after the lower rod 12c is raised, the fixing screw 12d may be tightened to adjust a length of the rod body 12 in the vertical direction.

Figure 5:
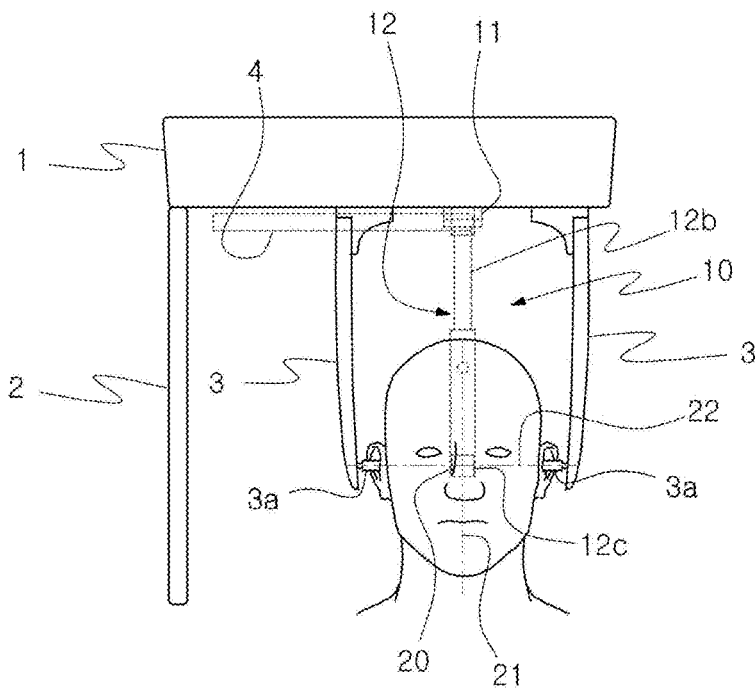
FIGS. 5 and 6 are reference diagrams illustrating the operation of the laser line projecting device for a lateral cephalometric radiograph device according to the present invention.

The projection unit 20 is provided to face toward the rear on a rear surface of the lower rod 12c, and as illustrated in FIG. 5, is configured to project a vertical line 21 extending in the vertical direction and a horizontal line 22 extending in a horizontal direction on a center of the user's face in a cross shape.

In this case, the projection unit 20 projects the vertical line 21 so as to extend from the center of the user's face fixed to the ear rod 3 in the vertical direction and projects the horizontal line 22 such that both ends thereof pass through the center of the ear plugs 3a.

To this end, the projection unit 20 is located in front of the ear plug 3a, and the horizontal line 22 projected from the projection unit 20 is horizontally projected to the rear side.

The projection unit 20 is the same as a laser level used in a construction site or the like, and thus a more detailed description thereof will be omitted.

A method of photographing a lateral cephalogram of the user using the laser line projecting device for a lateral cephalometric radiograph device will be described as follows.

First, in a state in which the support rod 10 is fixed to the support 1, and in a state in which the nasion guide 4 rotates in a lateral direction, the ear plugs 3a of the ear rods 3 are coupled to both ear holes of the user.

Further, when the projection unit 20 is turned on, the vertical line 21 and the horizontal line 22 are projected onto the user's face.

In this case, as the vertical line 21 is projected to extend from the center of the user's face in the vertical direction, an operator may check whether the head of the user is tilted to the left or right by visually identifying the vertical line 21. Further, when the head of the user is tilted to one side, the user may tilt the head to the left or right so that the head is vertically erect based on the left-right direction.

Further, as the horizontal line 22 is projected to pass through the center of the earplugs 3a, in a state in which the ear plugs 3a are coupled to the ear holes of the user, the user's head is tilted forward or backward such that the horizontal line 22 projected onto the ear plugs 3a passes through a lower side of the orbits of the user, and thus the user's head is vertically erect based on the front-rear direction.

Thus, in this way, after a position of the user's head is established based on the horizontal line and the vertical line in a state in which the ear plugs are not completely inserted, the generator may be turned on to obtain a lateral cephalometric image of the user.

Meanwhile, before the generator is turned on, the nasion guide 4 is brought into contact with the nasion of the user to check and photograph the front-rear tilt of the user's head.

The laser line projecting device for a lateral cephalometric radiograph device includes the support rod 10 extending downward from the lower surface of the support 1 of the lateral cephalometric radiograph device and the projection unit 20 provided on the support rod 10 and projecting linear light onto the user's face fixed to the ear rods 3, and the projection unit 20 projects the vertical line 21 extending in the vertical direction and the horizontal line 22 extending in the horizontal direction.

Thus, the operator may visually check the vertical line 21 to identify whether a central line of the user' face is accurately located on a sagittal plane, may photograph the head in a state in which the user' head is adjusted to be exactly perpendicular to the left-right direction and the front-rear direction, and thus may obtain an accurate lateral cephalometric image.

Figure 6:
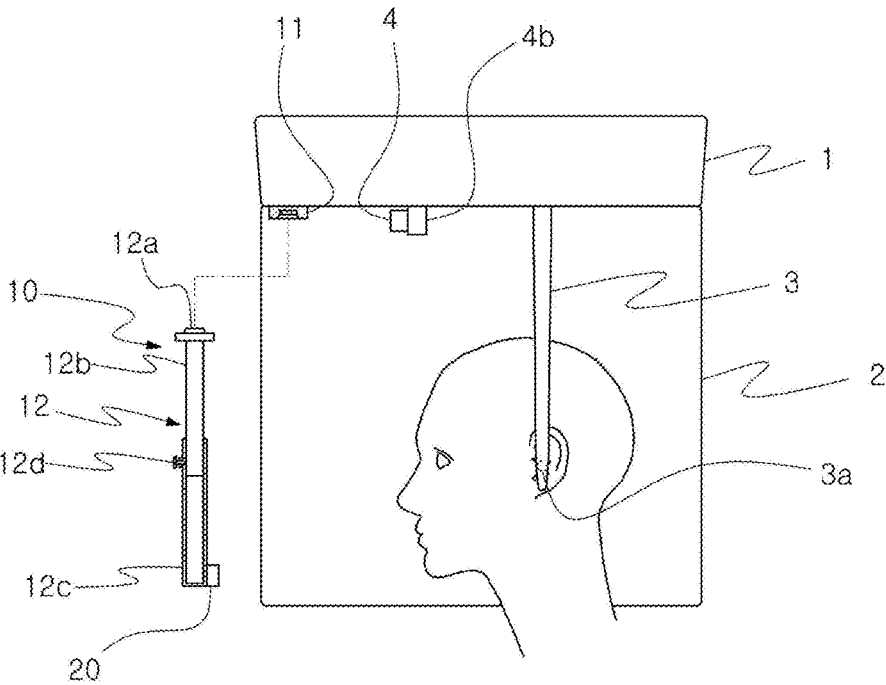

Further, the support rod 10 includes the fixed block 11 fixed to the lower surface of the support 1 and the rod body 12 extending in the vertical direction and having an upper end detachably coupled to the fixed block 11. Thus, when the nasion guide 4 is used, as illustrated in FIG. 6, the rod body 12 may be separated, and thus it is possible to prevent use of the nasion guide 4 from becoming cumbersome.

Further, the projection unit 20 may project the horizontal line 22 such that the horizontal line 22 passes through the center of the ear plugs 3a and thus may easily and vertically adjust the front-rear tilt of the user's head.

In the above embodiment, the support rod 10 includes the fixed block 11 fixed to the lower surface of the support 1 and the rod body 12 extending in the vertical direction and having an upper end detachably coupled to the fixed block 11, but the support rod 10 may be fixed so as not to be separated from the lower surface of the support 1.

Further, it is illustrated that the projection unit 20 projects the vertical line 21 extending in the vertical direction and the horizontal line 22 extending in the horizontal direction on the center of the user' face in a cross shape, but the projection unit 20 may project only one of the vertical line 21 and the horizontal line 22.

Figure 7:
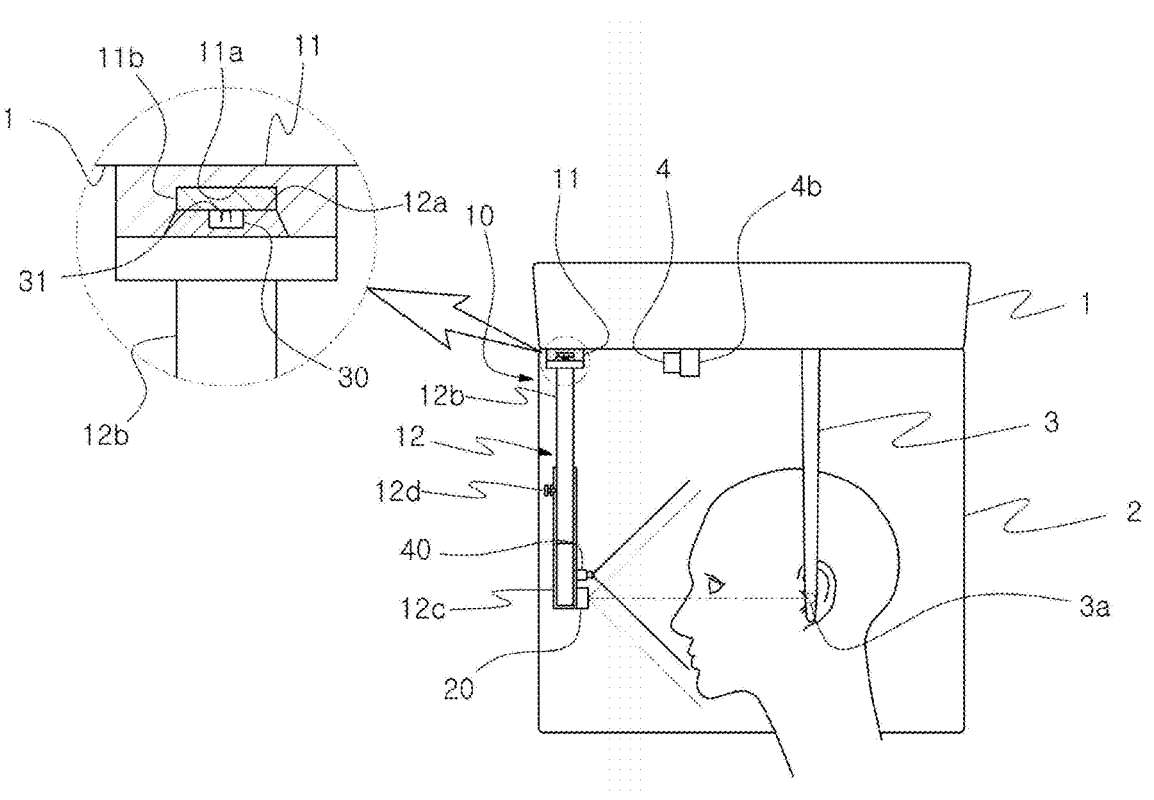
FIG. 7 is a side cross-sectional view illustrating a laser line projecting device for a lateral cephalometric radiograph device according to a second embodiment of the present invention.
Figure 8:
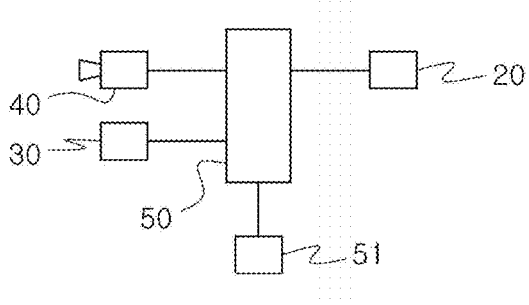
FIG. 8 is a block diagram illustrating the laser line projecting device for a lateral cephalometric radiograph device according to the second embodiment of the present invention.

FIGS. 7 and 8 illustrate another embodiment of the present disclosure, and the laser line projecting device further includes a coupling detecting unit 30 that is provided at an upper end of the rod body 12 and detects whether the rod body 12 is coupled to the fixed block 11, a camera 40 that is provided on the lower rear surface of the rod body 12 to face the rear and photographs the user's face and locations of the vertical line 21 and the horizontal line 22 projected onto the face, and a control unit 50 that is connected to the coupling detecting unit 30 and the camera 40 and controls the operation of the projection unit 20.

The coupling detecting unit 30 uses a limit switch provided with a push button 31 that protrudes upward and is provided on the upper end of the rod body 12, that is, on the upper surface of the coupling part 12a.

Thus, when the coupling part 12a is coupled to the coupling hole 11a of the fixed block 11, the push button 31 may be pushed to detect that the rod body 12 is coupled to the fixed block. Conversely, when the coupling part 12a is separated from the coupling hole 11a, the push button 31 may protrude upward to detect the separation.

The camera 40 is fixed to the rear surface of the lower rod 12c to be located above the projection unit 20 and is configured to photograph the user's face, particularly, the eye area, coupled to the ear rod 3.

The control unit 50 is equipped with an image analysis program 51 for analyzing an image captured by the camera 40.

The operation of the laser line projecting device for a lateral cephalometric radiograph device will be described as follows.

When the user turns on the projection unit 20, the control unit 50 receives a signal of the coupling detecting unit 30, and when it is detected that the upper end of the rod body 12 is separated from the fixed block 11, the projection unit 20 is turned off.

Further, when the user's face is photographed by the camera 40, the control unit 50 analyzes the photographed image through the image analysis program 51 and turns off the projection unit 20 when it is detected that light output from the projection unit 20, particularly, the horizontal line 22, is projected onto a location close to the user's eyes.

Thus, in a state in which the projection unit 20 is turned on so that light is projected onto the user's face, when the rod body 12 is unintentionally separated from the fixed block 11 or there is a risk of light being projected into the user's eyes due to the user moving his/her face, the protrusion unit 20 is automatically turned off, and thus an eye injury, which occurs when strong light is projected into the user's eyes, can be prevented.

DRAWING NUMBER 10. support rod
20. projection unit

The invention claimed is:

1. A laser line projecting device for a lateral cephalometric radiograph device, which is provided in the lateral cephalometric radiograph device including a support (1), a detector (2) extending downward from one side of the support (1), and ear rods (3) extending downward from the support (1) and adapted to be coupled to both ear holes of a user, the laser line projecting device comprising:

a support rod (10) extending downward from a lower surface of the support (1), wherein the support rod (10) includes:

a fixed block (11) fixed to the lower surface of the support (1); and a rod body (12) extending in the vertical direction and having an upper end detachably coupled to the fixed block (11);

a projection unit (20) provided on the support rod (10) and configured to project linear light onto a face of the user adapted to be fixed to the ear rods (3), wherein the projection unit (20) projects a vertical line (21) extending in a vertical direction adapted to pass through a center of the user's face or a horizontal line (22) extending in a horizontal direction passing through a midpoint determined by both of ear plugs which are adapted to be coupled to the ear holes of the user;

a coupling detecting unit (30) provided at an upper end of the rod body (12) and configured to detect whether the rod body (12) is coupled to the fixed block (11);

a camera (40) provided on a lower rear surface of the rod body (12) to face a rear side and configured to photograph the user's face and locations of the vertical line (21) or the horizontal line (22) projected onto the face; and a control unit (50) connected to the coupling detecting unit (30) and the camera (40) and configured to control operation of the projection unit (20), wherein the control unit (50) is equipped with an image analysis program (51) for analyzing an image captured by the camera (40) and turns off the projection unit (20) when it is detected through the coupling detecting unit (30) that the upper end of the body rod (12) is separated from the fixed block (11) or it is detected by analyzing the image captured by the camera (40) that light output from the projection unit (20) is projected to a location close to the user's eyes.

2. The laser line projecting device of claim 1, wherein the ear rods (3) are configured in a bar shape extending in the vertical direction and have the ear plugs (3*a*) extending in a lateral direction at a lower end thereof.

\*    \*    \*    \*    \*